United States Patent [19]

Yoshida et al.

[11] Patent Number: 4,760,265

[45] Date of Patent: Jul. 26, 1988

[54] METHOD AND DEVICE FOR DETECTING DEFECTS OF PATTERNS IN MICROELECTRONIC DEVICES

[75] Inventors: Akihiro Yoshida, Toyoake; Takahide Iida; Hiroshi Miyake, both of Obu; Shuzo Hattori, 42-1, Musashizuka, Nagakute, Nagakute-cho, Aichi-gun, Aichi-ken, all of Japan

[73] Assignees: Kabushiki Kaisha Toyoda Jidoshokki Seisakusho, Kariya; Shuzo Hattori, Aichi, both of Japan

[21] Appl. No.: 3,572

[22] Filed: Jan. 15, 1987

[30] Foreign Application Priority Data

Jan. 18, 1986 [JP] Japan ................................ 61-008391
Sep. 27, 1986 [JP] Japan ................................ 61-228980

[51] Int. Cl.⁴ ............................................. G01N 23/18
[52] U.S. Cl. .................................... 250/492.2; 378/34;
378/208; 378/210; 250/358.1; 250/363 R;
250/442.1; 250/491.1
[58] Field of Search .................... 378/34, 35, 208, 210;
250/440.1, 442.1, 491.1, 492.2, 492.3, 492.24, 4,
358.1, 363 R, 366; 324/158 R, 158 D, 73 PC, 73 R

[56] References Cited

U.S. PATENT DOCUMENTS

| | | | |
|---|---|---|---|
| 3,742,229 | 6/1973 | Smith et al. | 378/34 |
| 3,843,916 | 10/1974 | Trotel et al. | 250/492.24 |
| 4,260,670 | 4/1981 | Burns | 378/34 |
| 4,335,313 | 6/1982 | Krenzer et al. | 378/34 |
| 4,467,211 | 8/1984 | Smith et al. | 250/492.2 |
| 4,559,603 | 12/1985 | Yoshikawa | 250/492.2 |
| 4,613,981 | 9/1986 | Siddall et al. | 378/34 |

OTHER PUBLICATIONS

"Submicron Lithography" Author Unknown, published by Science forum in 1985, pp. 413–436, partial translation.

Primary Examiner—Craig E. Church
Assistant Examiner—John C. Freeman
Attorney, Agent, or Firm—Brooks, Haidt, Haffner & Delahunty

[57] ABSTRACT

An inspecting method and device for inspecting an object or objects such as photomasks having a plurality of identical patterns, to detect defects of the patterns, wherein the object is placed such that the patterns lie in the same plane, and an inspection mask having a plurality of translucent apertures is placed such that the inspection mask is adjacent and parallel to the object. The inspection mask and the object are moved relative to each other whereby each aperture is positioned opposite to mutually corresponding portions of the patterns. The object and inspection mask are irradiated with rays of light emitted in a direction substantially normal to the plane of relative movements thereof. The rays of light transmitted through the apertures and the object are converted into electric signals, and the electric signals associated with the corresponding portions of the patterns are compared with each other, prior to obtaining the electric signals of all of the plurality of patterns. If the electric signals of the corresponding portions of the patterns differ from each other, these portions are determined to be defective.

24 Claims, 12 Drawing Sheets

62: LENS POSITIONING CONTROLLER

METHOD AND DEVICE FOR DETECTING DEFECTS OF PATTERNS IN MICROELECTRONIC DEVICES

BACKGROUND OF THE INVETION

1. Field of the Invention

The present invention relates to a method of detecting defects or imperfections of patterns formed on an object substrate or substrates such as lithography masks used in the microfabrication of various microelectronic devices. The invention also relates to a device suitable for practicing such a detecting method.

2. Discussion of the Prior Art

Inspection to detect defects or imperfections of patterns formed on a substrate is required in various fields of technology. Typically, such inspection is carried out to detect defects of lithography masks, and reticles used to produce such photomasks.

A method of detecting defects of reticles is disclosed in "Submicron lithography (General Technical Treatise), page 425, published by Science Forum, in 1985. According to the disclosed method, design data of a reticle is processed into reference data which represents a pattern that consists of an aggregate of minute picture elements. Inspection data obtained as a result of inspection of a pattern of an actually produced reticle is compared with the reference data, whereby the pattern of the produced reticle is inspected for any defects. In this method, however, a computer used for the data comparison requires a memory having a large capacity, since all of the reference data must be stored in the memory. In the case where the inspection data representative of the inspected reticle pattern is temporarily stored in the memory, the required memory capacity is doubled. In particular, where the object to be inspected is masks used in x-ray photolithography, which is increasingly practiced in the industry, the lines forming a pattern are often less than one micron in thickness, and the size of the picture elements tends to be accordingly small. This indicates an enormous amount of data representative of the pattern. For example, the required memory capacity amounts to 62.5 giga bytes, where an area of $50 \times 50$ mm$^2$ is divided into picture elements of $0.2 \times 0.2$ $\mu$m$^2$.

The inspection of objects other than x-ray photolithography masks does not involve such an enormous amount of data. At any rate, it is desirable to minimize the required memory capacity, in order to reduce the cost of equipment for inspecting the objects.

The above-identified "Submicron lithography (General Technical Treatise)" also discloses at pages 417–419 an inspecting method in which two patterns are concurrently scanned by respective two laser beams or fluxes. The thus obtained two sets of data are compared with each other, and corresponding portions of the two patterns are determined to be defective if the data representative of one of the two corresponding portions critically differs from that of the other portion. This method eliminates a large-capacity memory. In this respect, the method contributes to lower the cost of the inspecting equipment. However, the use of two laser beams requires two separate optical systems, and makes the inspecting equipment cmplicated. While it is also possible to concurrently scan an increased number of patterns for increasing the inspecting efficiency, this approach needs an accordingly increased number of optical systems. Therefore, the number of the laser beams within an actually justifiable range is necessarily limited.

While the inspecting methods for detecting defects of patterns of photolithography masks and recticles have been discussed, there exist similar problems in the field of inspecting patterns of other kinds of objects such as printed-circuited boards.

SUMMARY OF THE INVENTION

It is accordingly an object of the present invention to provide an inspecting method for detecting defects of patterns, which uses a single optical system capable of concurrently scanning a plurality of points on the patterns, and which does not require a large-capacity memory.

Another object of the invention is the provision of an inspecting device suitable for practicing the above inspecting method.

According to the present invention, there is provided an inspecting method for inspecting at least one planar object having a plurality of patterns which should be identical with each other, in order to detect defects of the patterns, comprising the steps of: placing the at least one object such that all of the plurality of patterns lie in a single plane; perparing an inspection mask having a plurality of translucent apertures; placing the inspection mask such that the inspection mask is adjacent and parallel to the above-indicated at least one object; moving the inspection mask and the at least one object relative to each other in a plane parallel to the single plane, and positioning each of the apertures opposite mutually corresponding portions of the plurality of patterns, one after another in the same sequence; irradiating the above-indicated at least one object and the inspection mask with rays of light emitted in a direction substantially normal to the plane of relative movement thereof; coverting the rays of light which have been transmitted through the apertures and the at least one object or which have passed through the apertures and have been reflected by a surface of the at least one object, into electric signals by means of photo-electric converting means; comparing the electric signals associated with the corresponding portions of the plurality of patterns, with each other, prior to obtaining the electric signals of all of the plurality of patterns; and determining that the corresponding portions of the patterns have a defect if the electric signals thereof differ from each other.

In the method of the present invention described above, it is possible to scan a plurality of points on the same object or different objects with a single optical system, by moving the inspection mask having the plurality of translucent apertures, and the at least one object (substrate on which the patterns are formed), relative to each other. Consequently, the inspection to detect defects of the patterns may be accomplished with improved efficiency, with a comparatively inexpensive inspecting device using a simple optical system.

If the case where the plurality of apertures concurrently scan the corresponding portions of the patterns that should be identical with each other, electric signals simultaneously obtained as a result of the scanning may be instantaneously compared with each other. In the case where the electric signals associated with the corresponding portions of the patterns are obtained at different times, the inspecting device does not require a large capacity memory. In other words, only a small-capacity memory is required to store a relatively small amount of inspection data (electric signals) which covers a time difference between the times at which the electric signals of the corresponding portions of the patterns are obtained. In this respect, the cost of the inspecting equipment may be reduced.

The predetermined number of translucent apertures may be provided for each of the plurality of patterns that should be identical with each other. In this case, each aperture is used to scan a portion of one of the patterns. Alternatively, the plurality of patterns that should be identical with each other may be divided into a plurality of pattern groups, and one aperture may be provided for each pattern group. Although it is most convenient to simultaneously obtain electric signals associated with corresponding portions of the patterns and instantly compare these electric signals, this arrangement is not essential. Namely, it is possible that the electric signals of the corresponding portions of the patterns are obtained at different times. In this instance, the electric signal obtained earlier is maintained by use of shift registers or other means, until the other corresponding electric signal is later obtained, whereat the two signals are compared with each other.

According to an advantageous feature of the invention, the plurality of translucent apertures of the inspection mask consist of a plurality of aperture arrays corresponding to said plurality of patterns. The apertures in each array are disposed in mutually perpendicular x-axis and y-axis directions, so as to correspond to respective rectangular elementary inspection areas on the at least one planar object. Each of the rectangular elementary inspection areas has x-axis and y-axis dimensions which correspond to spacings between the adjacent apertures. The inspection mask and the at least one object are moved relative to each other in the x-axis and y-axis directions by respective distances equal to the x-axis and y-axis dimensions of each elementary inspection area, so as to irradiate an entire portion of each elementary inspection area sequentially and intermittently at x-axis and y-axis pitches equal to x-axis and y-axis dimensions of each of the apertures, whereby the elementary inspection areas are all concurrently inspected so that an entire area of each of the patterns is inspected.

The present invention is particular effective where three or more patterns are compared with each other, by using three or more translucent apertures provided on the inspection mask. In this case wherein three or more electric signals obtained are compared with each other, one of the corresponding portions of the three or more patterns is determined to be defective if the electric signal corresponding to that one portion of one of the three or more patterns is different from the other signals associated with the other patterns.

The instant inspecting method is suitable for inspecting photolithography masks, and particularly effective when the inspection is effected with x-rays, to inspect x-ray photolithography masks.

According to the present invention, there is also provided an inspecting device for inspecting at least one planar object having a plurality of patterns which should be identical with each other, in order to detect defects of the patterns, comprising: (a) an object support member for supporting the at least one object such that all of the plurality of patterns lie in a single plane; (b) an inspection-mask support member for supporting an inspection mask having a plurality of translucent apertures, such that the inspection mask is adjacent and parallel to the at least one object; (c) a positioning device for moving the inspection mask and the at least one object relative to each other in planes parallel to the single plane, and positioning each of the apertures opposite mutually corresponding portions of the plurality of patterns, one after another in the same sequence; (d) an irradiating device for irradiating the at least one object and the inspection mask with rays of light emitted in a direction substantially normal to the plane of relative movement thereof; (e) photo-electric converting means including a plurality of photo-electric converting elements corresponding to each of the translucent apertures, for converting into electric signals the rays of light which have been transmitted through each said aperture and the at least one object or which have transmitted through the apertures and have been reflected by a surface of the at least one object; (f) an optical system through which the rays of light transmitted through the apertures and the at least one object or reflected by the surface of the at least one object are incident upon the plurality of photo-electric converting elements of the photo-electric converting means; (g) determining means for comparing the electric signals associated with the corresponding portions of the plurality of patterns, with each other, and determining that the corresponding portions of the patterns have no defect if the electric signals thereof coincide with each other, and determining that the corresponding portions of the patterns have a defect if the electric signals thereof differ from each other; and (h) memory means for storing first position data indicative of one of the plurality of photo-electric converting elements which corresponds to the different electric signals indicative of the defect, and second position data indicative of a relative position between the at least one object, and one of the apertures which corresponds to the different electric signals, the memory means storing the first and second position data in corresponding relation with each other.

The number of said plurality of transparent apertures of the inspection mask may preferably be greater than the number of the plurality of patterns to be checked, but may be equal to or smaller than the number of the patterns.

The inspecting device of the invention constructed as described above provides the same advantages as offered by the method of the invention, as described above. In addition, the inspection data indicative of the positions of the detected defects of the inspected patterns are stored in the memory means. Therefore, the instant device makes it possible to correct or eliminate the detected defects, based on the stored inspection data, after the inspection of the object or objects is over. Since only the defect data indicative of the positions of the detected defect is required to be stored, the required capacity of the memory means is relatively small, whereby the cost of the inspecting device is accordingly reduced.

The instant inspecting device is suitable particularly for detecting defects of patterns which have a line thickness as small as one micron or lower, such as those produced by x-ray lithography technique. In this case, the optical system includes a scintillator for converting x-rays transmitted through the apertures and object or objects, into visible rays of light, and a lens system for directing the visible rays of light to photo-electric converting elements.

BRIEF DESCRIPTION OF THE DRAWINGS

The above and other objects, features and advantages of the present invention will be better understood by reading the following detailed description of preferred embodiments of the invention, when considered in conjunction with the accompanying drawings, in which.

DETAILED DESCRIPTION OF THE PREFERRED EMBODIMENTS

Referring to the accompanying drawings, there will be described in detail the preferred embodiments of the invention adapted to detect defects of x-ray photolithography masks.

Figure 1:
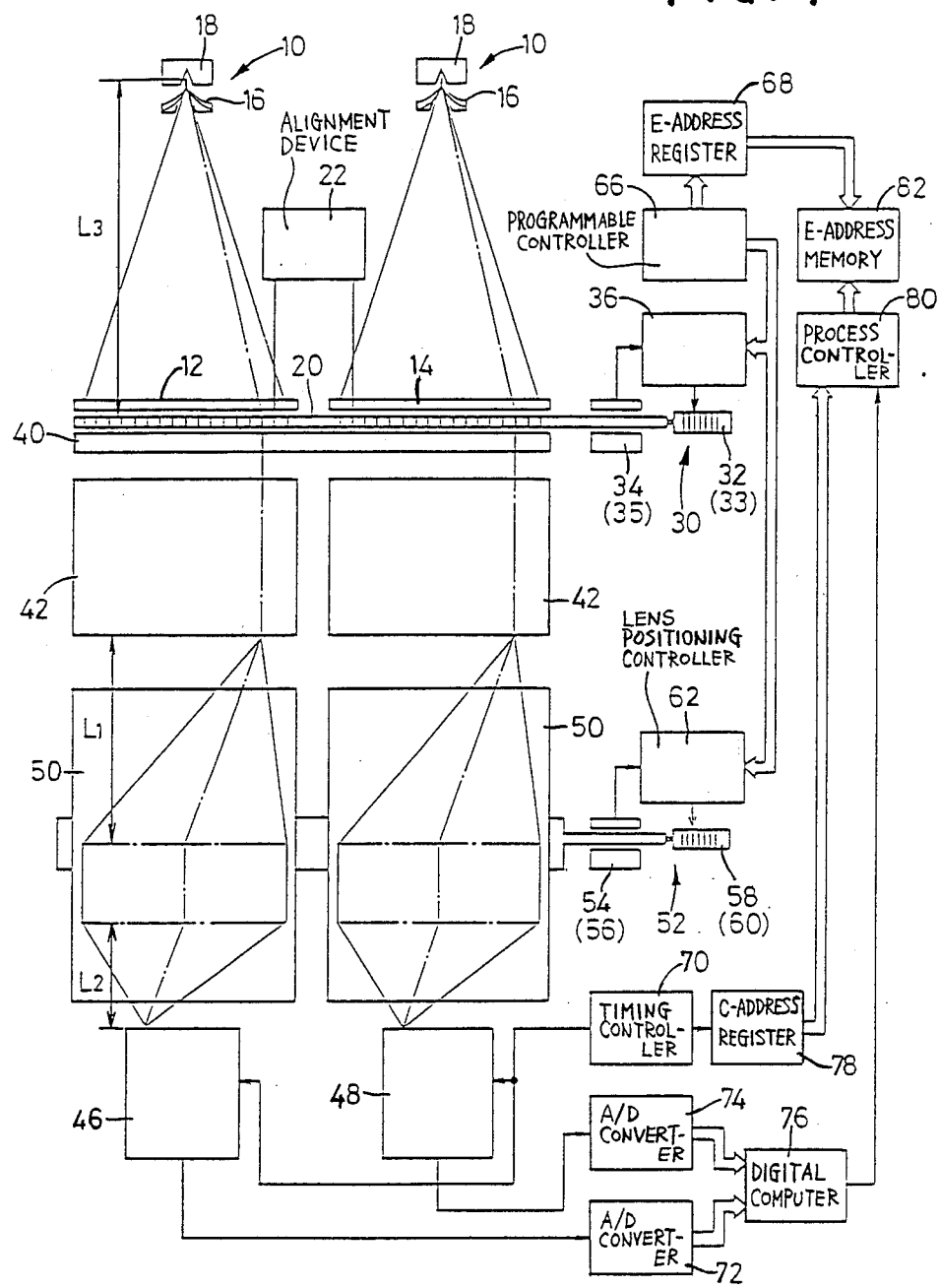
FIG. 1 is a schematic view of one embodiment of the present invention in the form of an inspecting device for detecting defects of photolithographically produced masks.

There is shown in FIG. 1 an arrangement for inspecting two photolithography masks, by way of comparing the masks with each other by using a single inspection mask.

The present arrangement of an inspecting device employs two x-ray sources 10, which emit x-rays for irradiating two objects in the form of two masks 12, 14 (hereinafter referred to as "object masks"). Each of the object masks 12, 14 comprises a substrate in the form of a glass plate or other transparent plate, and a thin metal film which forms circuit patterns. The instant device is adapted to inspect these circuit patterns. As the x-ray sources 10, are suitably used high-brightness x-ray sources as disclosed by Alfred Zacharias, in "IEEE Transacation on Components Hybrids and Manufacturing Technology", vol. CHMT-5, No. 1, March, 1982. The disclosed x-ray source uses an electron-beam gun 16 which emits high-voltage electrons, and a conical hollow target 18 which is irradiated with the electrons emitted by the gun 16. The conical hollow target 18, which has an effective diameter of 4 mm, excites the electrons up to 6 Kw, and produces a flux of $7.6 \times 10^{11}$ photons of 2.84 KeV, per sec. per $cm^2$ at a distance of 320 mm.

The object masks 12, 14 are supported by a support device provided with a support member (object-mask support member) whose position can be finely adjusted. With the support device, the object masks 12, 14 are positioned above an inspection mask 20. The inspection mask 20 has two arrays of translucent x-ray apertures (which transmit x-rays) 26 which are formed by electron-beam lithography. Each array consists of $n_x \times n_y = 384 \times 485$ x-ray apertures 26 (where $n_x$=number of apertures in the x direction, and $n_y$=number of apertures in the y direction). Each aperture 26 has dimensions of $\delta \times \delta = 0.5$ $\mu m \times 0.5$ $\mu m$. The apertures 26 of each array are arranged two-dimensionally, at pitches of $Xe \times Ye = 184$ $\mu m \times 108$ $\mu m$ (where $Xe$=pitch in the x direction, and $Ye$=pitch in the y direction).

The object masks 12, 14 and the inspection mask 20 are positioned relative to each other by an alignment device 22. The alignment device 22 is equipped with a detector for detecting a phase difference of moire gratings formed on the object masks 12, 14 and inspection mask 20. The above-indicated object-support member is operated so that the output signal of the detector coincides with a predetermined value. With this fine adjustment in the position of the masks 12, 14 with respect to the inspection mask 20, desired portions of the masks 12, 14, i.e., picture elements 24 in each elementary inspection area 25 that are inspected first are aligned with the corresponding x-ray apertures 26 on the inspection mask 20.

Figure 2:
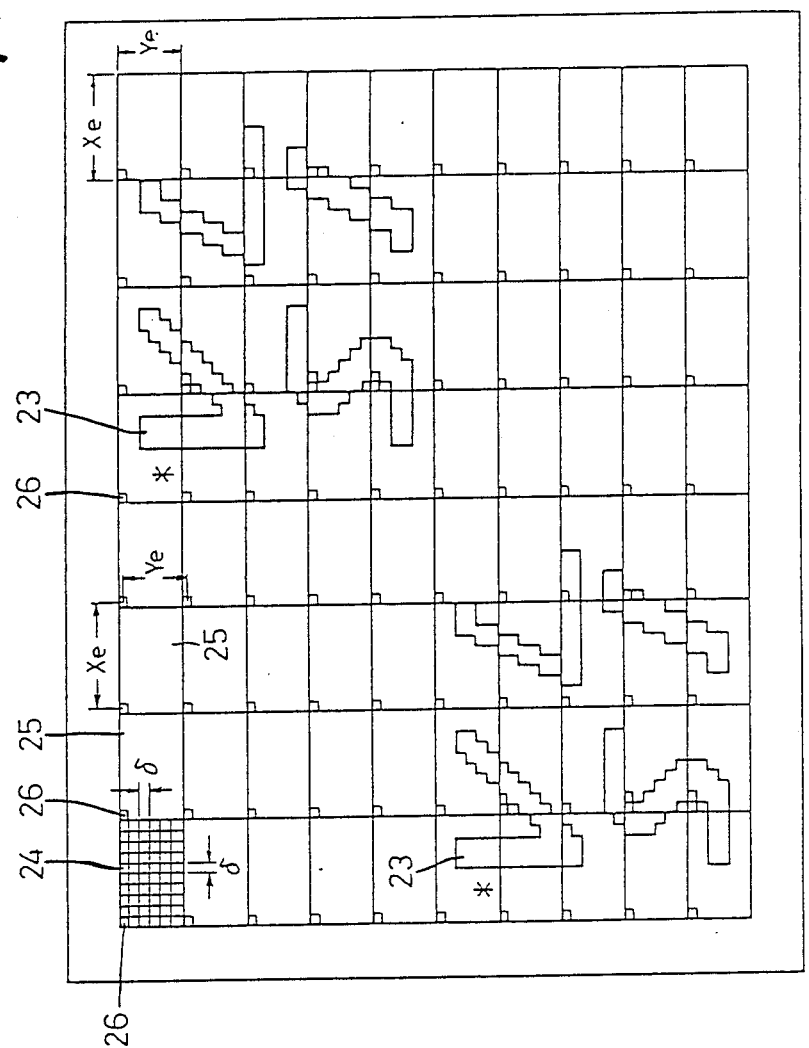
FIG. 2 is an explanatory view showing a relative position between an inspection mask and an object mask under inspection.

Referring next to FIG. 2, there is illustrated a state in which the object mask 12 and the inspect mask 20 are exactly aligned with each other. For easier understanding, the figure uses alphabetic letters to show patterns 23, and the numbers of picture elements 24 and elementary inspection areas 25 are extremely reduced as compared with those of a actually produced mask. The object mask 12 is illustrated as if the entire body was an transparent object.

Each picture element 24 is a square having a length of each side equal to a design rule $\delta$. The x-ray aperture 26 has the same dimensions as the picture element 24. Each elementary inspection area 25 consists of $m_x \times m_y = 368 \times 216$ picture elements 24.

The inspection mask 20 has a total of $n_x \times n_y = 384 \times 485$ x-ray apertures 26. The spacings of the apertures 26 in the x and y directions are equal to the x-axis and y-axis dimensions of the elementary inspection area 25. Described in greater detail, the x-ray apertures 26 are formed at intersections of a plurality of parallel, spaced-apart first straight lines parallel to the x axis, and a plurality of parallel, spaced-apart second straight lines parallel to the y axis perpendicular to the x axis, the straight lines being equally spaced from each other by distances of Xe and Ye in the x-axis and y-axis directions, respectively. When the object masks 12, 14 are precisely aligned with the inspection mask 20, each x-ray aperture 26 of the inspection mask 20 is aligned with the picture element 24 at the upper left corner of the corresponding elementary inspection area 25. From this position, the inspection mask 20 is moved intermittently in increments of $\delta$ in the x and y directions, the numbers of intermittent movement in the x and y directions being equal to $m_x$ and $m_y$, respectively, whereby all of the picture elements 24 in each elementary inspection area 25 are sequentially aligned with the corresponding x-ray aperture 26. The object masks 12, 14 are disposed parallel to the inspection mask 20, with a proximity gap of 10 μm maintained therebetween.

The inspection mask 20 is moved in the mutually perpendicular x and y directions by a mask-positioning device (first positioning device) 30. Described more specifically, the inspection mask 20 lies in a plane normal to a direction in which the mask 20 is irradiated by the x-rays radiated by the X-ray sources 10. The mask 20 is moved in that plane in the mutually perpendicular x and y directions. The first positioning device 30, which will be described in detail, incorporates two piezoelectric actuators 32, 33 for moving the inspection mask 20 in the x and y directions. These peizoelectric actuators 32, 33 are controlled by a positioning controller 36 which receives feedback signals from moire encoders 34, 35. Under the control of the positioning controller 36, the actuators 32, 33 are operated to move the inspection mask 20 intermittently in the x and y directions in steps by a distance equal to the length of each side of the picture element 24, that is, $\delta = 0.5$ μm. To enable each x-ray aperture 26 to scan the picture elements 24 of the corresponding elementary inspection area 25 having dimensions of $Xe \times Ye = 184$ μm $\times 108$ μm (determined by the spacings of the apertures 26 in the x and y directions), the positioning controller 36 designates a total of $m_x \times m_y = 368 \times 216$ E-addresses.

A total of $384 \times 485$ x-ray images of each object mask 12, 14 corresponding to the x-ray apertures 26, are converted into visible light images by a scintillator in the form of a scintillation crystal 40. Two groups of the visible light images of the two object masks 12, 14 are intensified by respective image intensifers 42, 42, to a sufficiently high level so that the charge-coupled devices (CCD) 46, 48 (charge-coupled elements) may process received image signals even in the presence of noises. The image intensifiers 42, 42 are adapted to increase the intensity of images received at their input surfaces, and produce the intensified images from their output surfaces. Since the function of the image intensifiers is well known in the art, no detailed description thereof will be provided.

Figure 3:
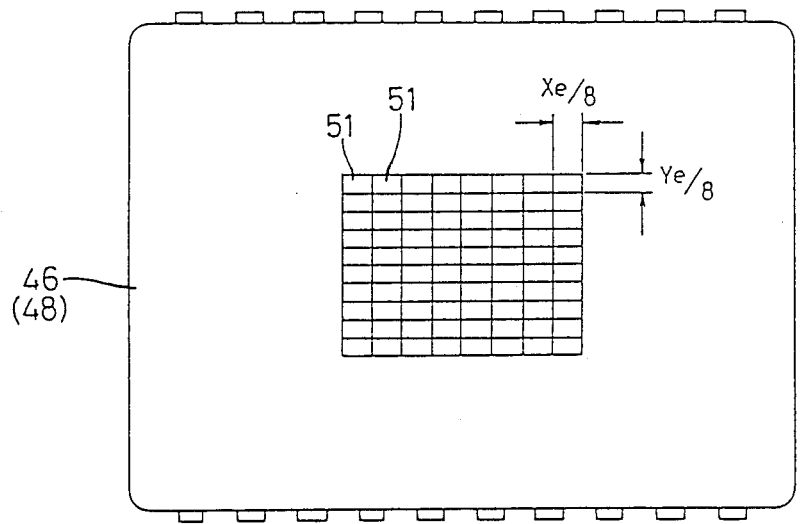
FIG. 3 is an illustration of a CCD used in the inspecting device of FIG. 1, schematically showing an arrangement of light-sensitive elements of the CCD.

The intensified visible light images at the output surfaces of the image intensifiers 42 are condensed by respective lens systems 50, 50, and focused on the surfaces of the CCDs 46, 48. Each CCD 46, 48 has a total of $n_x \times n_y = 384 \times 485$ photo-electric converting elements in the form of an array of light-sensitive elements 5 schematically illustrated in FIG. 3 (the number of the elements illustrated being less than that of an actually produced CCD). The light-sensitive elements 51 have dimensions equal to their pitches of arrangement in the x and y directions. By selecting a suitable demagnification ratio of the lens system 50, i.e., a suitable ratio of a first focal length L1 to a second focal length L2 of the lens system 50, the x and y pitches of the visible light images incident upon each lens system 50 may be made equal to the pitches of the light-sensitive elements 51 of the corresponding CCD 46, 48. In the instant specific example, the demagnification ratio is selected at ⅛, so that two-dimensional pitches of $Xe \times Ye = 184$ μm $\times 108$ μm of the visible light rays are reduced to two-dimensional pitches of 23 μm $\times 13.5$ μm of the light-sensitive elements 51. In this arrangement, the $384 \times 485$ images from each of the two arrays of the x-ray apertures 26 are focused or concentrated on the corresponding $n_x \times n_y = 384 \times 485$ light-sensitive elements 51 of the corresponding CCD 46, 48.

The lens systems 50, 50 are moved by a lens-positioning device (second positioning device) 52, in synchronization with the first positioning device 30 for moving the inspection mask 20. The reason for this synchronization will be described below:

Firstly, the focusing accuracy of the optical images from the x-ray apertures may be sometimes intentionally made lower than is actually possible, or the optical images are intentionally defocused to some extent, in order to prevent saturation of the light-sensitive portion of each light-sensitive element 51 of the CCD 46, 48. Secondly, the lens systems 50 will more or less distort the optical images from the $n_x \times n_y$ array of the x-ray apertures 26. While the inspection mask 20 scans the picture elements 24 in each elementary inspection area 25 under such conditions, the images from the x-ray apertures 26 may deviate from the corresponding light-sensitive elements 51 of the CCDs 46, 48. To avoid this deviation and precisely focus each image at a central portion of the corresponding light-sensitive element 51, the lens systems 50 are moved by the second positioning device 52, being synchronized with the movement of the inspection mask 20.

Like the first positioning device 30 for moving the inspection mask 20, the second positioning device 52 is provided with moire encoders 54, 56, and piezoelectric actuators 58, 60, for the movements of the lens systems 50 in the x and y directions. These encoders 54, 56 and the actuators 58, 60 are connected to a lens positioning controller 62, which controls the positioning device 52 so as to move the lens systems 50, 50 in increments of ⅛ of each intermittent movement of the inspection mask 20 by the first positioning device 30.

There will be next described a control system for controlling the operation of the instant inspecting device. The control system is substantially constituted by a computer whose functional elements are schematically indicated by blocks in FIG. 1, for easier understanding of the operation of the control system.

In the present embodiment, different kinds of inspection masks are prepared, which are selectively used as the inspection mask 20. While the apertures 26 described above have the dimensions of $\delta \times \delta = 0.5$ μm $\times 0.5$ μm, the apertures 26 formed on the other inspection masks 20 have different dimensions $\delta$, which are multiples of the above value of 0.5 μm. The inspecting resolution of the inspecting device may be changed in steps by changing the inspection mask 20 to be used. To permit the use of such different kinds of inspection masks 20, control programs to control an E-address register 68 and the positioning controllers 36, 62 are changed, by a programmable controller 66 connected thereto, so that the increment of movements of the inspection mask 20 is changed depending upon the size of the x-ray apertures 26 on the selected mask 20. It is noted, however, that the following description applies to the inspecting device when operated with the inspection mask 20 having the x-ray apertures 26 of 0.5 μm $\times 0.5$ μm.

The CCDs 46, 48 are connected to a timing controller 70, so that outputs of the CCDs 46, 48 are retrieved when the inspection mask 20 is positioned such that each x-ray aperture 26 is located at a position corresponding to the E-address which is currently selected in the E-address register 68 by the programmable controller 66. The timing controller 70 regulates the timings at which serial signals indicative of the x-ray images are obtained from the two CCDs 46, 48. More specifically, the timing controller 70 permits concurrent retrieval of two inspection signals, i.e., two x-ray image signals (indicative of visible light images converted from the x-ray images) of the corresponding picture elements 24, 24 of the two object masks 12, 14, from the two CCDs 46, 48. The x-ray image signals obtained from the CCDs 46, 48 are converted into digital x-ray image data by respective A/D converters 72, 74. The digital data from the A/D converter 74 is compared with that from the other A/D converter 76, by a digital computer 76. If these two sets of data have a difference exceeding a predetermined limit, the digital computer 76 generates a DEFECT signal.

The timing controller 70 is also connected to a C-address register 78 which stores C-addresses indicative of two-dimensional positions of the light-sensitive elements 51 of the CCDs 46, 48. Each time a timing signal is received from the timing controller 70, the C-address register 78 gives a newly selected C-address to a process controller 80. The process controller 80, which also receives the DEFECT signal from the digital computer 76, applies the C-address received from the C-address register 78, to an E-address memory 82 upon reception of the DEFECT signal from the digital computer 76. The E-address memory 82 has memory areas for storing a suitable number of C-addresses which are designated by the E-addresses. That is, the C-addresses from the process controller 80 are sequentially stored in the memory areas of the E-address memory 82 which are designated by the E-address register 68.

After the outputs of the light-sensitive elements 51 of each CCD 46, 48 which represent the first picture elements 24 of the individual elementary inspection areas 25 have been obtained, the programmable controller 66 designates the next E-address in the E-address register 68, and controls the positioning controller 36 to increment the inspection mask 20 so that the individual x-ray apertures 26 are aligned with the next picture elements 24 in the corresponding elementary inspection areas 25. At the same time, the programmable controller 66 controls the positioning controller 62 to move the lens systems 50 in synchronization with the inspection mask 20. At the end of this positioning of the inspection mask 20 and the lens systems 50, the timing controller 70 is activated to control the times at which the serial image signals are retrieved from the CCDs 46, 48.

Figure 4:
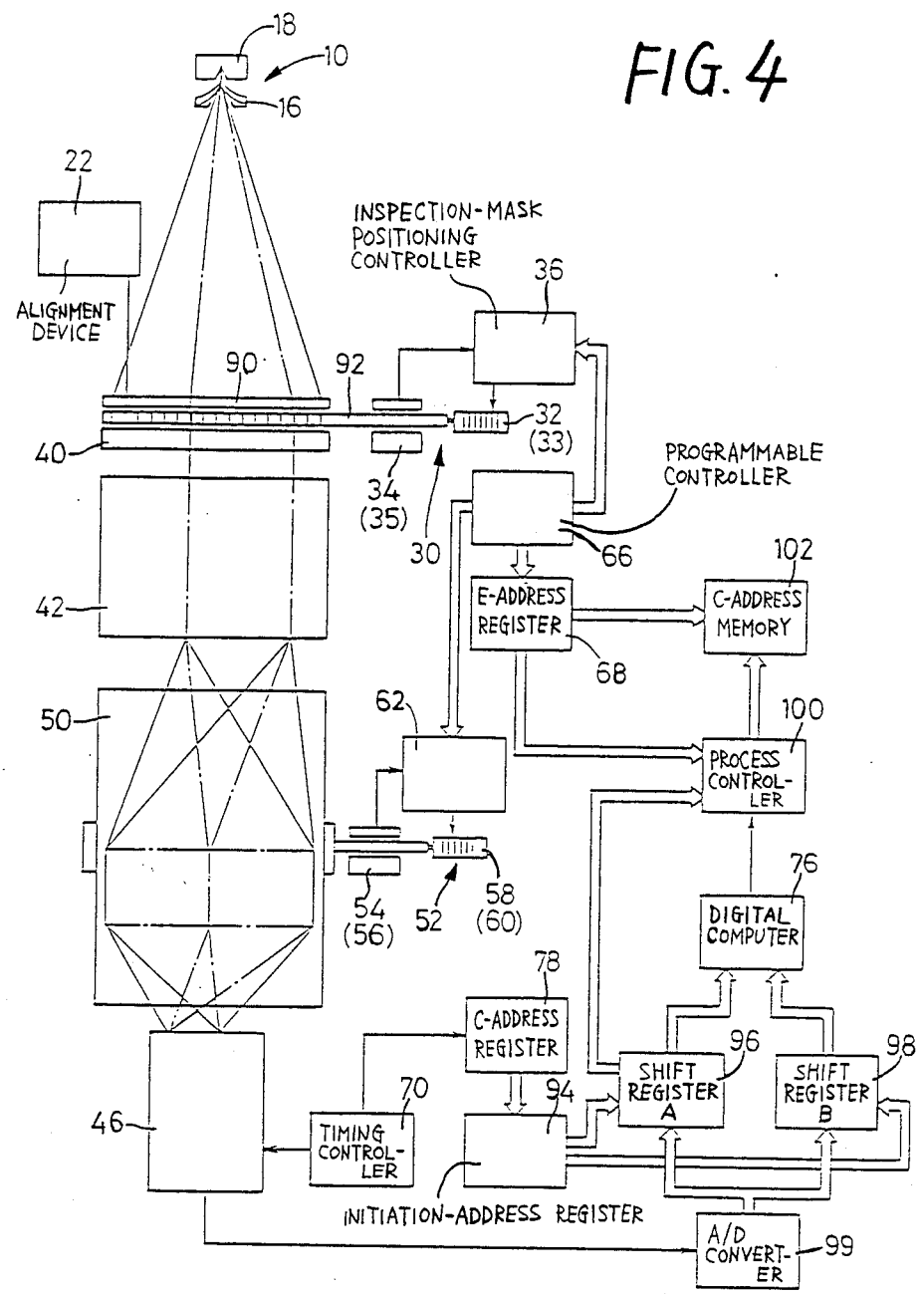
FIG. 4 is a schematic view of another embodiment of an inspecting device of the invention for detecting defects of photolithographically produced masks.

Referring to FIG. 4, there is shown another embodiment of the present invention adapted to detect defects of identical patterns (circuit patterns) which are formed on a single object or substrate (glass plate).

Since this modified inspecting device is similar to the preceding embodiment in a number of points, the same reference numerals as used in the preceding figures are used to identify the similar components or elements, and redundant description of which is omitted. As such, the following description refers only to such parts of the instant modified device which differ from those of the preceding embodiment.

An object mask 90 to be inspected has at least two patterns 23 that should be identical with each other (as indicated in FIG. 2), while an inspection mask 92 has an array of x-ray apertures 26 as provided on the inspection mask 20.

The elementary inspection areas 25, 25 initiation inspection areas) including portions of the two identical patterns 23, 23 that are inspected first, are designated as (nx1, ny1) and (nx2, ny2). Further, the two x-ray apertures 26, 26, (nx1, ny1) and (nx2, ny2) corresponding to the designated initiation inspection areas 25, 25 are selected from the $n_x \times n_y$ apertures, and the object mask 90 is positioned by the alignment device 22 such that the designated initiation inspection areas 25, 25 are precisely aligned with the corresponding x-ray apertures 26, 26. In FIG. 2, these two initiation inspection areas 25, 25 are indicated by "*" marks.

Subsequently, the inspection mask 92 and the lens systems 50 are synchronously moved to sequentially scan the picture elements 24 in the two inspection areas 25. Serial image signals are obtained from the CCD 46, in the same manner as described above in connection with the preceding embodiment. In the present embodiment, however, an initiation-address register 94 is provided in addition to the C-address register 78. The initiation-address register 94 stores C-addresses indicative of the two light-sensitive elements 51 of the CCD 46 which correspond to the two initiation inspection areas 25, 25, that is, the initiation-address register 94 stores initiation-addresses (nx1, ny1) and (nx2, ny2). The initiation-address register 94 is operated to obtain C(A) address and C(B) address, by subtracting the initiation addresses (nx1, ny1) or (nx2, ny2) from the C-address received from the C-address register 78. The obtained C(A) and C(B) addresses are applied to a shift register A 96 and a shift register B 98, respectively.

The serial image signals from the CCD 46 are converted into a series of digital parallel signals by an A/D converter 99. The digital image signals from the A/D converter 99 are applied to the shift registers A and B 96, 98. The shift registers 96, 98 select from the received series of image signals from the CCD 46, image signals relating to the two patterns A and B, according to the C(A) and C(B) addresses, and applies the corresponding two sets of image data having the same C(A) and C(B) addresses, to the digital computer 76.

If the received two sets of image data have a difference over a predetermined limit, the digital computer 76 applies a DEFECT signal to a process controller 100. In the meantime, a delayed C(A) address corresponding to the x-ray image data whose C(A) address is compared, is produced in the shift register A 96, and is delivered to the process controller 100. Upon reception of the DEFECT signal from the digital computer 76, the process controller 100 stores in a C-address memory 102 the E-address indicative of the defective picture elements, according to the delayed C(A) address received. More specifically, the memory areas of the C-address memory 102 are designated by the C-addresses, and the E-address currently selected in the E-address register 68 is stored in the memory area of the C-address memory 102 which is designated by the delayed C(A) address supplied from the shift register A 96 when the process controller 100 receives the DEFECT signal from the digital computer 76. In the preceding embodiment, the C-addresses indicative of the light-sensitive elements 51 of the CCD 46, 48 which have detected a defect are stored in the E-address memory 82 having the memory areas which are designated by the E-addresses indicative of the positions of the picture elements 24 on the object masks 12, 14. To the contrary, the instant embodiment is adapted such that the E-addresses indicative of the positions of the picture elements 24 on the object mask 90 are stored in the C-address memory 102 whose memory areas are designated by the C-addresses indicative of the positions of the light-sensitive elements 51 of the CCD 46. In either case, the E-address and C-address selected at the time a defect is detected are stored in corresponding relation with each other, so that the position of the defect may be recognized.

It is possible to replace the C-address memory 102 of the instant embodiment by a serial memory, so that the process controller 100 stores into the serial memory DEFECT data which consists of a pair of E-address and C(A) address each time the process controller 100 receives the DEFECT signal from the digital computer 76.

Figure 5:
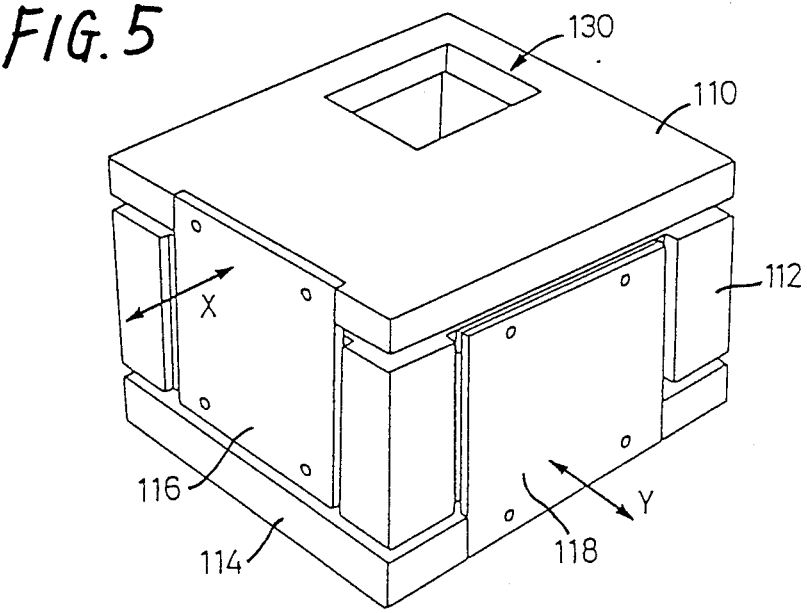
FIG. 5 is a perspective view of an x-y positioning unit having x- and y-motion members, used in the inspecting devices of FIGS. 1 and 4.

Referring now to FIGS. 5 through 8, there will be described the first positioning device 30. As seen in FIG. 5, the device 30 is of a three-stage construction including an upper stage 110 (second movable member), an intermediate stage 112 ((first movable member), and a lower stage 114 (base). With the mechanism explained below, the upper stage 110 is accurately displaceable in the x and y directions over a maximum distance of 200 μm.

Figure 6:
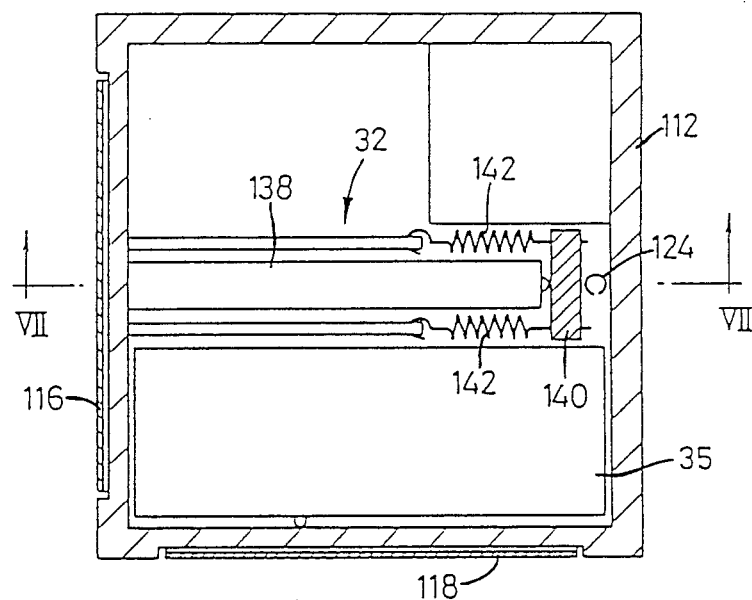
FIG. 6 is a plan view in cross section of the x-y positioning unit (cross sectional view taken along line VI—VI of FIG. 7)
Figure 7:
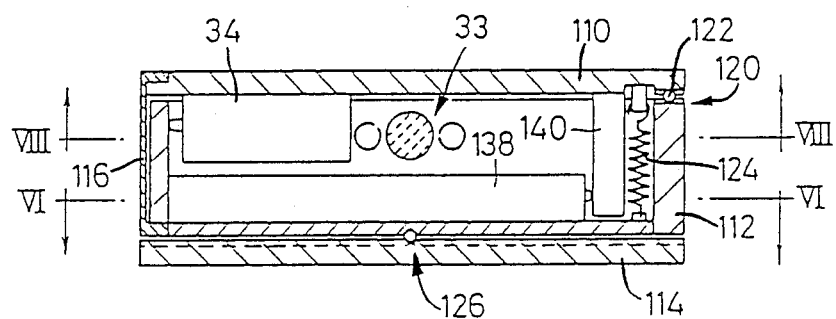
FIG. 7 is a cross sectional view taken along line VII—VII of FIG. 6.
Figure 8:
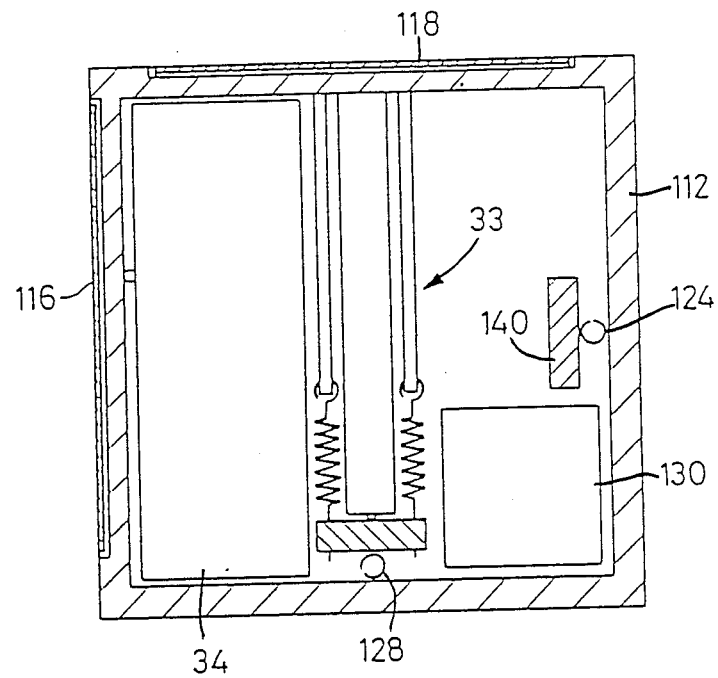
FIG. 8 is a cross sectional view taken along line VIII—VIII of FIG. 7.

The intermediate stage 112 has a rectangular hollow structure which has wide, shallow grooves formed in the two adjacent outer surfaces so as to extend in the vertical direction (in the direction perpendicular to the plane of FIG. 6). These grooves accommodate respective sheet springs 116, 118 such that the springs are spaced away from the side and bottom surfaces of the grooves. The upper end of the sheet spring 116 is fixed to one of opposite ends of the upper stage 110, while the lower end of the sheet spring 116 is secured to the lower end of the intermediate stage 112. Thus, the upper stage 110 is supported at its one end by the intermediate stage 112, so that the upper and intermediate stages 110, 112 are movable relative to each other in a direction perpendicular to the plane of the sheet spring 116, with elastic deformation of the spring 116. As shown in FIG. 7, the end of the upper stage 110 opposite to the above-indicated one end supported by the sheet spring 116 is supported by the intermediate stage 112 via a ball bearing 120. Balls 122 of the ball bearing 120 are retained in a retainer (not shown) and are received in paallel V-grooves formed in the lower surface of the upper stage 110 and the upper surface of the intermediate stage 112. The ball bearing 120 is held in pressed rolling contact with the upper and intermediate stages 110, 112, with a biasing force of a spring 124 connected to the two stages 110, 112. The arrangement described above permits the upper stage 110 to be moved relative to the intermediate stage 112, with a slight rolling friction resistance. Although it is possible to flexibly connect the upper stage 110 at its opposite ends to the intermediate stage 112 by two sheet springs similar to the spring 116, it is desirable that the upper stage 110 is supported at its one end with the ball bearing 120, since a suitable degree of rolling friction of the ball bearing 120 improves the stability of displacement of the upper stage 110.

Similarly, the intermediate stage 112 is connected to the lower stage 114 by the sheet spring 118, a ball bearing 126 and a spring 128, such that the intermediate stage 112 is displaceable relative to the lower stage 114. The direction of movement of the upper stage 110 is perpendicular to the direction of movement of the intermediate stage 112. Consequently, the upper stage 110 connected to the intermediate stage 112 is movable in the mutually perpendicular x and y directions. The inspection masks 20, 92, etc. are mounted by means of a suitable fastener, at an opening 130 formed in the upper stage 110, as shown in FIG. 5. Thus, the masks 20, 92, etc. are moved in the x and y directions, together with the upper stage 110. In the present embodiment, the lower stage 114 serves as a base of the positioning device 30, on which the intermediate and upper stages 112, 110 are supported as a first and a second movable member, respectively. Further, the upper stage 110 and the above-indicated fastener cooperate to function as a support member for supporting the inspection mask 20, 92.

The upper stage 110 is moved in the x direction by the piezoelectric actuator 32 (second actuator). A major portion of the actuator 32 consists of a piezoelectric stack 138 of a multiplicity of piezoelectric elements. The piezoelectric stack 138 is secured at its one end to the intermediate stage 112, as seen in FIGS. 6 and 7. The other end of the stack 138 is held in abutting contact with a driven portion 140 fixed to the upper stage 110. The piezoelectric stack 138 is pre-loaded with a predetermined compression force, by a pair of tension springs 142, in the direction toward the fixed end. The piezoelectric stack 138 has anodes and cathodes which are alternately disposed between the multiple piezoelectric elements. In operation, the stack 138 expands and contracts in response to a change in the level of voltages applied between the anodes and cathodes. Since this arrangement is well known in the art, no further description is deemed necessary. The intermediate stage 112 is driven in the y direction by the similarly constructed piezoelectric actuator 33 (first actuator).

Figure 9:
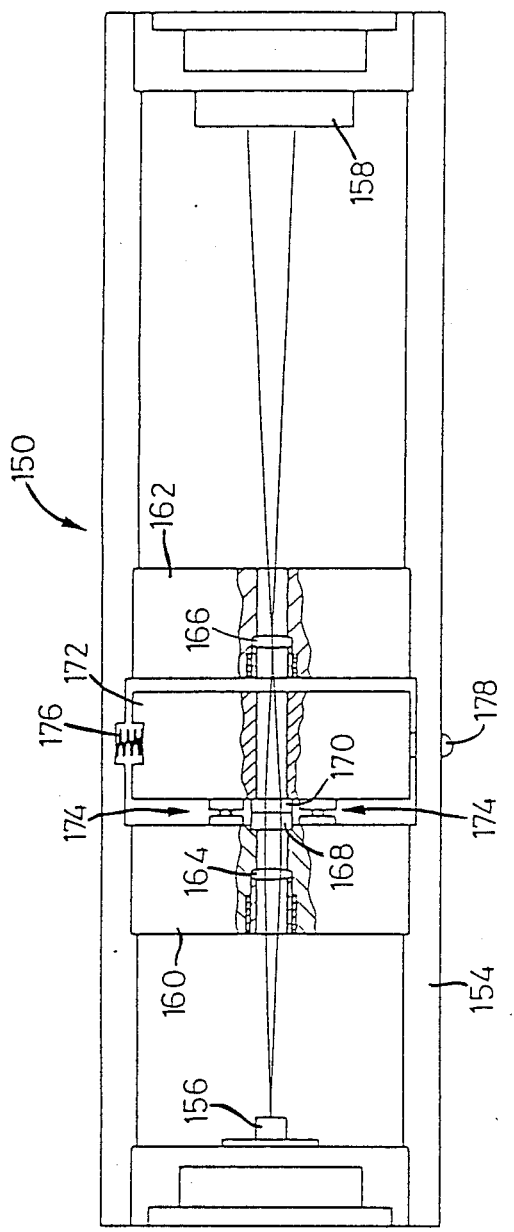
FIG. 9 is a plan view in cross section of a moire encoder incorporated in the x-y positioning unit of FIG. 5.

The amounts of movements of the upper and intermediate stages 110, 112 in the x and y directions are sensed by the moire encoders 34, 35 indicated above. These two moire encoders 34, 35 are identical in construction with each other. The construction of the encoders 34, 35 will be explained, referring to FIG. 9 which illustrates the arrangement of the encoder 34 which also applies to the encoder 35. The moire encoder 34 has a semiconductor laser 156 and a CCD (charge-coupled device) 158, which are mounted on a casing 154 such that the laser 156 and the CCD 158 are disposed in a mutually facing relation. A laser beam radiated by the semiconductor laser 156 is incident upon the CCD 158, through lenses 164, 166 which are received in holes formed through respective stationary blocks 160, 162. Between the two lenses 164, 166, there are disposed two moire gratings 168, 170. The moire grating 168 is fixed to the stationary block 160, and other other moire grating 170 is fixed to a movable block 172. The movable block 172 is biased toward a ball bearing 174 by two springs (not shown), and is supported movably perpendicularly to a direction of propagation of the laser beam. The movable block 172 is further biased by a spring 176 in one direction perpendicular to the direction of propagation of the laser beam, so that a contactor 178 fixed to the block 172 extends from the outer surface of the casing 154.

Figure 10:
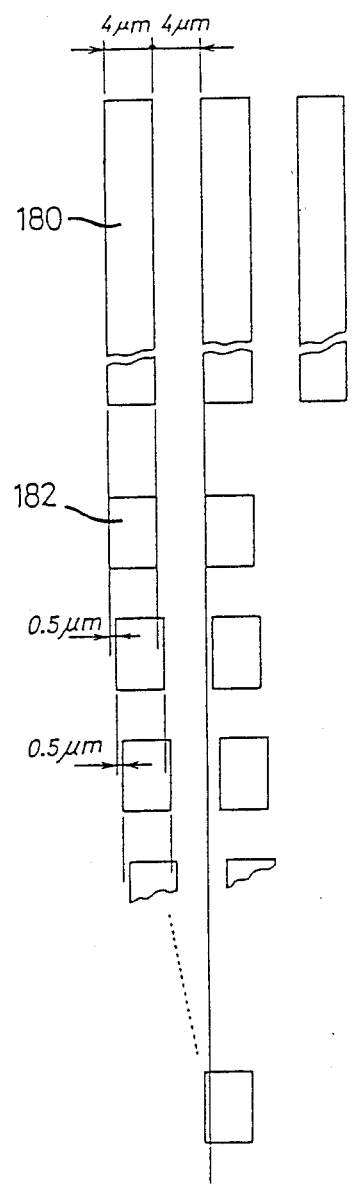
FIG. 10 is an explanatory view illustrating a moire grating of the moire encoder.

The moire grating 168 has a multiplicity of first apertures 180 having a width of 4 μm, as shown in the upper part of FIG. 10. The first apertures 180 are evenly spaced from each other by a distance of 4 μm, in the direction of width. The other moire grating 170 has a multiplicity of second apertures 182 as indicated in the lower part of FIG. 10. The second apertures 182 are spaced from each other in the direction of length of the first apertures 180. However, the adjacent second apertures 182 are offset from each other by a distance of 0.5 μm, in the direction of width of the first apertures 180. Described more specifically, the second apertures 182 are disposed in 16 parallel rows extending in the direction of width of the first apertures 180, such that the second apertures 182 in each row are displaced or offset from the corresponding first apertures 180 by a distance equal to 1/16 of the 8 μm spacing of the first apertures 180.

The CCD 158 has 16 rows of light-sensitive elements corresponding to the 16 rows of the second apertures 182 of the moire grating 170. The light-sensitive element of the CCD 158 which receives the laser beam from the row of the second apertures 182 exactly aligned with the first apertures 180, provides the highest output voltage. The output voltage of the light-sensitive elements of the CCD 158 are lowered with an increase in the offset distance between the first and second apertures 180, 182. The moire signals produced by the N-th and (N+8)-th light-sensitive elements N and (N+8) of the CCD 158 are fed back as error signals to the positioning controller 36. Based on a phase difference of the moire error signals, the positioning controller 36 is capable of controlling the piezoelectric actuator 32 with a positioning accuracy as high as 40 nm, i.e., 1/200 of the 8 μm spacing of the moire grating 168.

The moire encoder 34 is attached to the upper stage 110 such that its contactor 178 is in contact with the intermediate stage 112, as indicated in FIG. 7. As depicted in FIGS. 1 and 4, the moire encoder 34 is connected to the positioning controller 36, so that the output of the encoder 34 is fed back to the controller 36. In this arrangement, the upper stage 110 is moved in the x direction in increments of 0.5 μm, relative to the intermediate stage 112, and is positioned with an extremely high level of accuracy on the order of 0.01 μm.

It will be understood from the foregoing description that the illustrated embodiments of the invention are adapted to permit detection of defects of x-ray lithography masks (12, 14, 90) having a 0.5 μm design rule, by means of the high-brightness x-ray source 10, scintillator (scintillation crystal 40) and CCD 46, 48. In order to detect defects of a pattern having a 0.5 μm width, the detecting resolution must be no more than 0.2 μm. Hence, the defect detection of such a pattern is impossible with visible rays of light having comparatively long wavelengths.

Another feature of the present invention resides in the provision of a plurality of translucent x-ray apertures 26 in the inspection mask 20, 92, which makes it possible to achieve accurate defect detection of relatively large-sized object masks 12, 14, 90. Inspection of picture elements of 0.5 μm×0.5 μm requires positioning accuracy of 50 nm. This means that the inspection of a 50 mm×50 mm mask requires relative positioning precision as high as $10^{-6}$. According to the illustrated embodiments wherein the multiple x-ray apertures 26 are formed on the inspection mask 20, 92, the multiple elementary inspection areas 25 on the surface of the object masks 12, 14, 90 are scanned by the corresponding x-ray apertures 26. In this arrangement, the inspection mask 20, 92 is required to be positioned with sufficient precision, only within a range covering the elementary inspection area 25. Further, it is comparatively easy to form the multiple x-ray apertures 26 with a satisfactory degree of relative spacing precision. Therefore, the illustrated inspecting devices may fully satisfy the extremely stringent requirement for relative positioning accuracy of the inspection mask with respect to the object masks.

The x-y movable unit provided by the piezoelectric actuators 32, 33 in combination with the moire encoders 34, 35 provides positioning accuracy of 1/200 of the pitch of the moire gratings 168, 170, i.e., as high as 40 nm. While the positioning accuracy of the moire encoders 34, 35 are affected by the precision of the moire gratings 168, 170, it is not difficult to form the 2-mm moire gratings to within $10^{-5}$, or 20 nm precision, by utilizing the electron-beam micro-fabrication technology available in the present state of the art.

A positioning error at the edge of an inspection area of d×d cm² is obtained from the following formula:

$$\epsilon = (dG) \times d/2L3$$

where, (dG): fluctuation of the proximity gap between the inspection mask 20, 92 and the object masks 12, 14, 90, L3: distance between the x-ray source 10 and the inspection mask 20, 92.

Suppose d=50 mm, and L3=320 mm, the value (dG) must be 0.5 μm or lower, to maintain the value ε not more than 40 nm. This small gap fluctuation, or high stability of the proximity gap may be assured by the use of the x-y positioning device 30 which uses the ball bearings 120, 126 and the sheet springs 116, 118 for improved mechanical stability.

In the case where defects are detected by an electron-beam flying spot method, the inspection requires not only an x-y positioning device having $10^{-6}$ relative positioning accuracy of the inspection mask and the object mask for the total relative displacement, but also high electric and magnetic field stability in the electron beam column, high inspection timing accuracy, and as high as $10^{-6}$ mechanical accuracy or stability of the electron-beam column. In the present invention, however, the total inspecting precision and stability are affected by the mechanical stability or accuracy of the x-y positioning device for as small as 0.2 mm movement thereof, and the control accuracy of the positioning controller to control this short distance of movement of the positioning device.

Further, the illustrated embodiments using the high-brightness x-ray source or sources 10 as a light source permit a relatively high inspecting speed. The resolution Δ in the x-ray inspection is obtained from the following formula:

$$\Delta = G \times D/L3$$

where,

G: proximity gap,

D: diameter of the x-ray source (10)

L3: distance between the x-ray source (10) and inspection mask (20, 92).

In the case where G=10 μm, D=4 mm, and the width of a pattern to be inspected is 0.5 μm, the distance L3 should be 320 mm in order to ensure a resolution of 0.125 μm, which is one fourth of the 0.5 μm pattern width. A presently available 6 Kw high-brightness x-ray source gives a 0.35 mW per cm² flux at 320 mm distance, that is, produces $2.19 \times 10^{15} \times 0.35 \times 10^{-3} = 7.6 \times 10^{11}$ photons per sec. per cm² of 2.84 KeV (PdLα; λ=4.36 angstroms).

In the meantime, the signal-to-noise ratio (S/N) of a light-sensitive element is given by the following formula:

$$(S/N) = (\eta \phi \delta^2 \tau)^{\frac{1}{2}}$$

where, $\phi$: photon flux $\eta$: quantum efficiency of light-sensitive element $\delta$: length of each side of a square picture element $\tau$: time of exposure to the flux Accordingly, suppose $\eta=0.3$, $\tau=1/15$ sec., $\delta=5\times10^{-5}$, and $\phi=7.6\times10^{11}$, the S/N is equal to 6.2.

Each of the CCDs 46, 48 used in the illustrated embodiments has an $n_x \times n_y$ array of light-sensitive elements 51 each of which has a size of Xp×Yp. A corresponding $n_x \times n_y$ array of visible rays of light from the lens sytem 50 with a demagnification ratio of 1/N is focused on the corresponding $n_x \times n_y$ array of the light-sensitive elements 51 of the CCD 46, 48. The $n_x \times n_y$ x-ray apertures 26 each having a size of $\delta \times \delta$ cm$^2$ are formed on the inspection mask 20, 92, in equally-spaced relation with each other, with a spacing distance of Xe in the x direction and a spacing distance of Ye in the y direction. By positioning the inspection mask 20, 92, each of the x-ray aperture 26 is sequentially aligned with the mx×my picture elements 24 of a size of $\delta \times \delta$ cm$^2$ in the corresponding elementary inspection area 25 having a size of Xe×Ye=mx$\delta$×my$\delta$. The value N is determined so as to satisfy the equations: Xe=NXp, Ye=NYp. Accordingly, Nnx Xp×Nny Yp=nxmx $\delta$×nymy $\delta$ covers the whole area of the object mask 12, 14, 90. The nx x ny image signals from the CCD 46, 48 are parallel-processed or concurrently processed in a processing time of $\tau$. With this parallel processing repeated mx×my times, the total area of N$^2$ nx ny Xp Yp is inspected in a total inspection time of mx my $\tau$.

In the specific illustrated embodiments wherein the total inspection area is 71 mm×52 mm, the total inspection time is about 88 minutes, where:

$nx \times ny = 384 \times 485$ (number of apertures 26), $Xp \times Yp - 23$ $\mu$m×13.5 $\mu$m (size of light-sensitive element 51), N=8 (demagnification ratio of lens system 50), $\delta^2 = 0.5$ $\mu$m×0.5 $\mu$m (size of picture elements 24), $mx \times my = 368 \times 216$ (number of picture elements 24),
$Xe \times Ye = 184$ $\mu$m×108 $\mu$m (size of elementary inspection area 25),
$\tau = 1/15$ sec. (processing time).

Moreover, the illustrated embodiments do not require a large-capacity memory for storing pattern data representative of individual picture elements of a photolithographically produced mask pattern, but requires relatively small-capacity memory means (C-address memory 82, C-address memory 102) for storing defect data indicative of the positions of the detected defects. Described more particularly, the required minimum memory capacity is equal to a capacity necessary to store the E-addresses indicative of the positions of the picture elements 24 in the elementary inspection area 25, and the C-addresses indicative of the positions of the light-sensitive elements 51, multiplied by the number of the detected defects. Namely, the required minimum memory capacity is a product of the above-indicated capacity and the number of the detected defects.

In the embodiment of FIG. 4, the shift registers 96, 98 are used to compensate for a difference in the timing of detection of two sets of image data from the corresponding portions of the two patterns that should be identical with each other, in order to compare the two sets of image data with each other. However, the required maximum memory capacity of these shift registers 96, 98 is only $nx \times ny = 384 \times 485$ bytes.

The present invention may be embodied in other forms.

FIGS. 11 through 14 show modified embodiments wherein the objects to be moved by the first and second positioning devices 30, 52 are different from those of the embodiment shown in FIG. 4 (FIG. 4 embodiment).

These modified embodiments are similar to the FIG. 4 embodiment in many aspects. Therefore, the same reference numerals as used in FIG. 4 will be used in FIGS. 11-14 to identify the similar elements. Redundant description of these elements will not be provided. Instead, the following description refers only to those elements which are different from those of the FIG. 4 embodiment.

Figure 11:
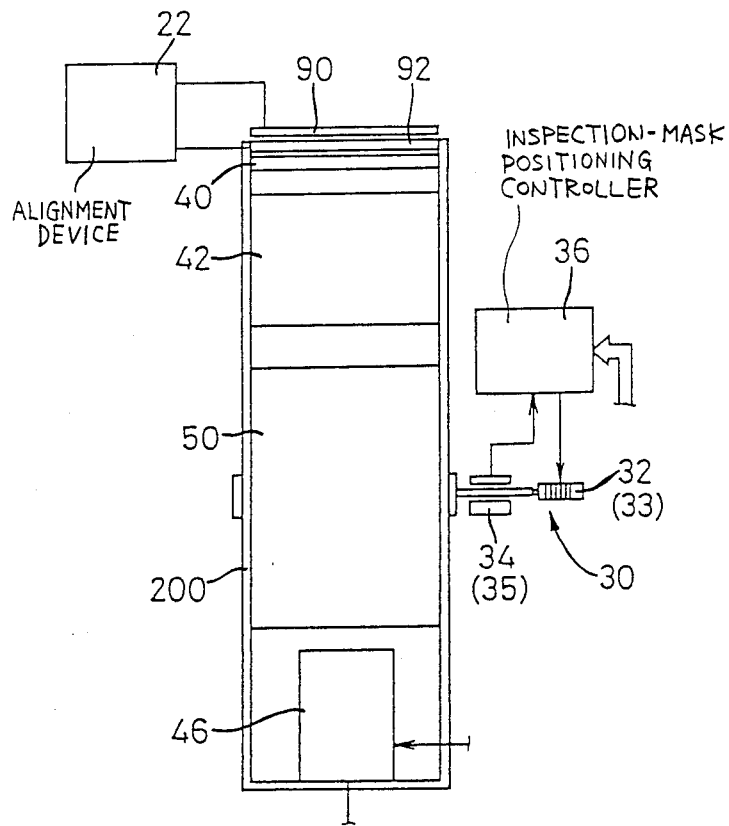
FIGS. 11–14 are fragmentary schematic views of further embodiments of the present invention, showing parts thereof which are different from the embodiment of FIG. 4.

The inspecting device of the embodiment shown in FIG. 11 uses a frame 200 which supports the inspection mask 92, scintillator 40, image intensifier 42, lens system 50 and CCD 46 as a unit. The frame 200 is connected to the positioning device 30, so that the scintillator 40, image intensifier 42, lens system and CCD 46 are moved together with the inspection mask 92 when the mask 92 is displaced relative to the object mask 90. Thus, the object to be moved by the positioning device 30 in this embodiment consists of the inspection mask 92, scintillator 40, image intensifier 42, lens system 50 and CCD 46. Thus, the present embodiment does not require a second positioning device (52) and a controller (62) therefor, as used in the FIG. 4 embodiment. This results in lowering the cost of the equipment. Further, the control system may be simplified, and the control accuracy may be improved, as compared with that for controlling the two positioning devices (30, 52).

Figure 12:
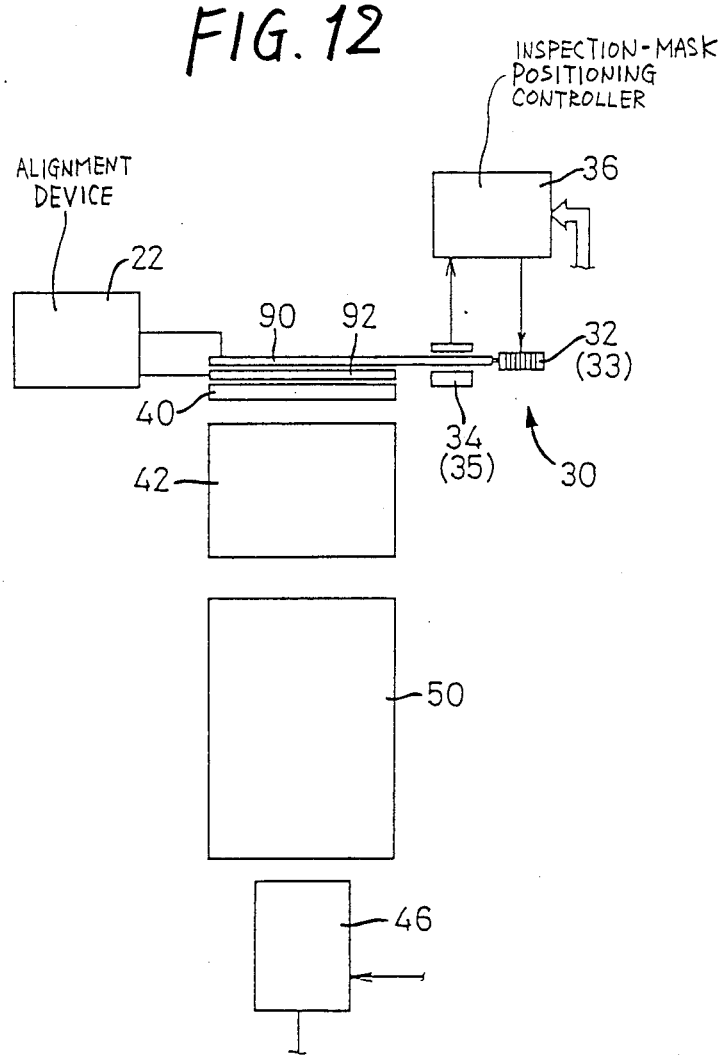

In the modified embodiment of FIG. 12, the inspection mask 92, scintillator 40, image intensifier 42, lens system 50 and CCD 46 are all fixed in position. The object mask 90 is moved relative to the fixed inspection mask 92. That is, the object to be moved by the positioning device 30 is the object mask 90. This alternative embodiment also eliminates a second positioning device (52) and a controller (62) therefor. Since the object to be moved by the positioning device 30 is relatively small and lightweight, the required capacity of the device 30 may be reduced. These two aspect contribute to lowering the cost of the inspecting device. Furthermore, the small size and weight of the object to be moved by the device 30 leads to improvement in the control accuracy.

Figure 13:
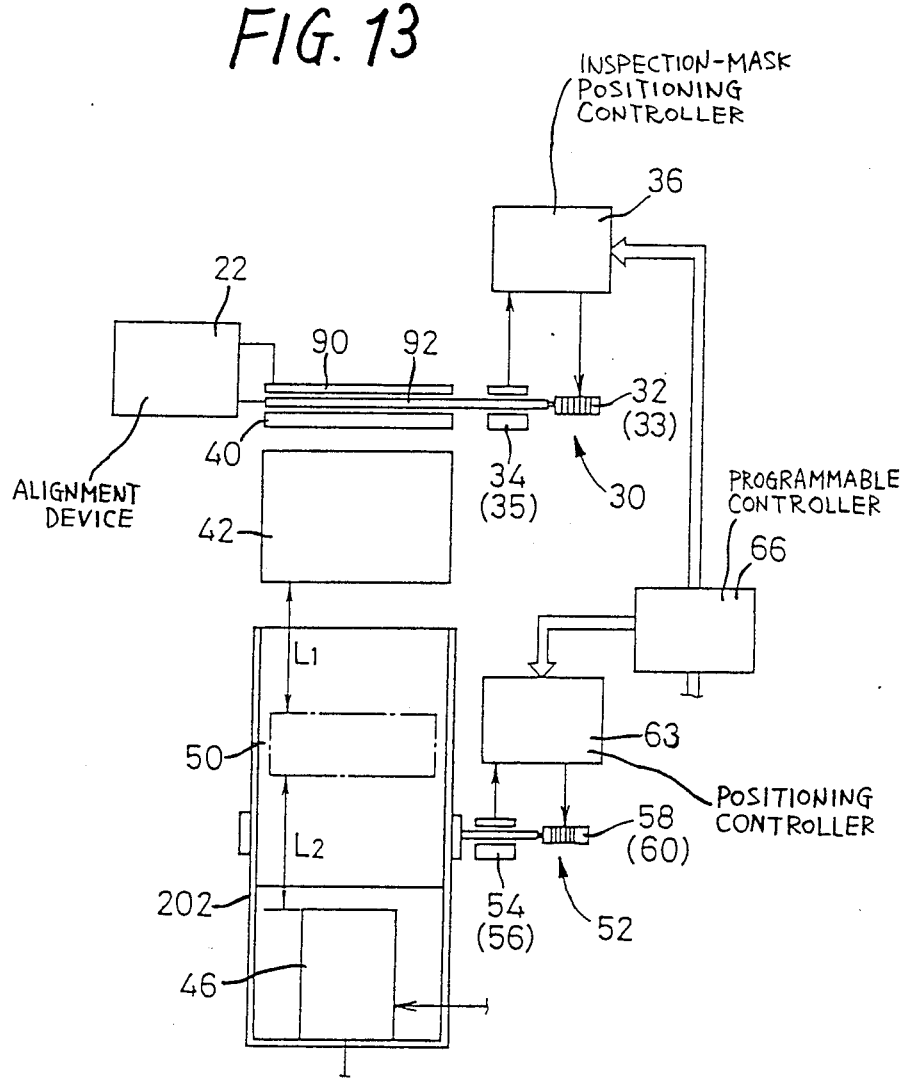

In the embodiment shown in FIG. 13, the CCD 46 is fixed to the lens system 50 by a frame 202, so that the CCD 46 and the lens system 50 are moved as a unit by the second positioning device 52. Namely, the object to be moved by the second positioning device 52 in this embodiment consists of the lens system 50 and the CCD 46. The first and second focal lengths L1 and L2 of the lens system 50 are determined so that the individual visible light images at the output surface of the image intensifier 42 are focused on the corresponding light-sensitive elements 51 of photo-electric converting means in the form of the CCD 46. The second positioning device 52 is operated in synchronization with the first positioning device 30, by the same amount, under the control of a positioning controller 63.

Figure 14:
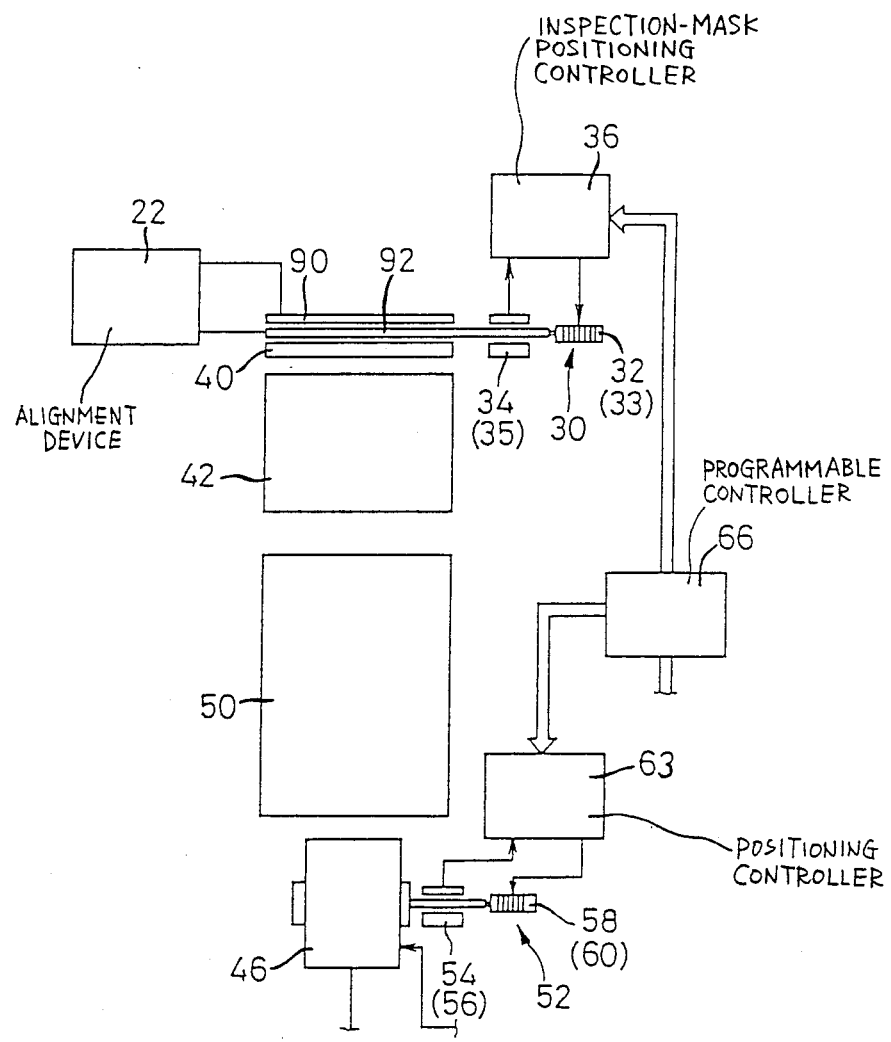

In the embodiment of FIG. 14, the positioning device 52 is used to move the CCD 46, rather than the lens system 50. In this case, too, the object to be moved is relatively small and lightweight, permitting the positioning device 52 to be small-sized. the second positioning device 52 is operated in synchronization with the first positioning device 30, under the control of the positioning controller 63.

The arrangements shown in FIGS. 11-14 are available even when the inspecting operation occurs on a plurality of object masks, as in the first embodiment of FIG. 1.

While the present invention is most effective for inspecting x-ray lithography masks which require extremely high inspecting resolution, the concept of the invention is also applicable to the detection of defects of masks used in photolithography utilizing visible rays of light, and further to the defect detection of patterns such as those on printed-circuit boards, and other patterns whose defect may be detected with a considerably low level of inspecting resolution, as compared with the patterns produced in photolithography. In the case where visible rays, ultraviolet rays or infrared rays are used to irradiate the object and inspection masks, the two-dimensionally disposed light-sensitive image sensing elements may be responsive to the rays reflected by the masks, as well as to the light which is transmitted through the translucent apertures of the inspection mask and the object mask.

The CCDs used in the illustrated embodiments as photo-electric converting means may be replaced by other solid image sensing elements such as MOS type image sensors, or industrial television cameras.

In the case where the required inspecting accuracy is not so high, an x-y table using stepping motors and ball screws and nuts may be used as a device for positioning the inspection and object masks relative to each other.

It will be understood that the present invention may be embodied with other changes, modifications and improvements which may occur to those skilled in the art, in the light of the foregoing teachings.

What is claimed is:

1. An inspecting method for inspecting at least one planar object having a plurality of patterns which should be identical with each other, in order to detect defects of the patterns, comprising the steps of:
   placing said at least one object such that all of said plurality of patterns lie in a single plane;
   preparing an inspection mask having a plurality of translucent apertures;
   placing said inspection mask such that the inspection mask is adjacent and parallel to said at least one object;
   moving said inspection mask and said at least one object relative to each other in a plane parallel to said single plane, and positioning each of said apertures opposite mutually corresponding portions of said plurality of patterns, one after another in the same sequence;
   irradiating said at least one object and said inspection mask with radiant energy emitted in a direction substantially normal to said plane of relative movement thereof;
   converting the radiant energy that both passes through said apertures and is transmitted through or reflected by a surface of said at least one object, into electric signals by means of radiant energy converrting means;
   comparing the electric signals associated with said corresponding portions of said plurality of patterns, with each other, prior to obtaining said electric signals of all of said plurality of patterns; and
   determining that said corresponding portions of said patterns have a defect if said electric signals thereof differ from each other.

2. An inspecting method according to claim 1, wherein said plurality of translucent apertures of said inspection mask consist of a plurality of aperture arrays corresponding to said plurality of patterns, said apertures in each array being disposed in mutually perpendicular x-axis and y-axis directions, and corresponding to respective rectangular elementary inspection areas on said at least one planar object, each of said rectangular elementary inspection areas having x-axis and y-axis dimensions which correspond to spacings between said apertures, said inspection mask and said at least one object being moved relative to each other in said x-axis and y-axis directions by respective distances equal to said x-axis and y-axis dimensions of said each elementary inspection area, so as to irradiate an entire portion of said each elementary inspection area sequentially and intermittently at x-axis and y-axis pitches equal to x-axis and y-axis dimensions of each of said apertures, so that said elementary inspection areas are all concurrently inspected so that an entire area of each of said patterns is inspected.

3. An inspecting method according to claim 1, wherein said plurality of patterns consist of at least three patterns, and said translucent apertures consist of at least three apertures, said electric signals to be compared with each other consisting of at least three electric signals, said step of determining comprising checking if any one of said at least three electric signals differs from the others, and if a signal differs, indicating that the corresponding one of said at least three patterns has a defect.

4. An inspecting method according to claim 1, wherein said at least one object having said plurality of patterns consits of at least one photomask used in photo-lithography.

5. An inspecting method according to claim 1, wherein said radiant energy consists of x-rays, said step of converting the radiant energy comprises converting said x-rays which have been transmitted through said translucent apertures and said at least one object, into visible rays of light, and converting said visible rays of light into said electric signals by means of photo-electric converting means.

6. An inspecting method according to claim 1, wherein said plurality of patterns are formed on a single object.

7. An inspecting method according to claim 1, wherein said plurality of patterns are formed on a plurality of separate objects.

8. An inspecting device for inspecting at least one planar object having a plurality of patterns in order to detect defects of the patterns, comprising:
   an object support member for supporting said at least one object such that all of said plurality of patterns lie in a single plane;
   an inspection mask support member for supporting an inspection mask having a plurality of translucent apertures, such that the inspection mask is adjacent and parallel to said at least one object;
   a positioning device for moving said support members relative to each other in a plane parallel to said single plane for positioning each of said apertures opposite mutually corresponding portions of said plurality of patterns, one after another in the same sequence;

an irradiating means for irradiating said at least one object and said inspection mask with radiant energy emitted in a direction substantially normal to said plane of relative movement thereof;

radiant energy converting means including a plurality of photo-electric converting elements corresponding to each of said translucent apertures, for converting into electric signals the radiant energy that both passes through said apertures and is transmitted through or reflected by a surface of said at least one object;

an optical system for imaging said radiant energy upon said plurality of photoelectric converting elements of said radiant energy converting means;

determining means for comparing the electric signals associated with said corresponding portions of said plurality of patterns, with each other, and determining that said corresponding portions of said patterns have no defect if said electric signals thereof coincide with each other, and determining that said corresponding portions of said patterns have a defect if said electric signals thereof differ from each other; and memory means for storing first position data indicative of one of said plurality of photo-electric converting elements which corresponds to the different electric signals indicative of said defect, and second position data indicative of a relative position between said at least one object and one of said apertures which corresponds to said different electric signals, said memory means storing said first and second position data in corresponding relation with each other.

9. An inspecting device according to claim 8, wherein said plurality of translucent apertures are disposed at respective intersections of a plurality of first parallel, equally spaced-apart straight lines formed on said inspection mask so as to extend in a first direction, and a plurality of second parallel, equally spaced-apart straight lines formed on said inspection mask so as to extend in a second direction perpendicular to said first direction, said radiant energy converting means comprising two-dimensionally disposed image-sensing elements which are equally spaced apart from each other in said first and second directions, by a distance proportional to the spacing of said apertures in said first and second directions.

10. An inspecting device according to claim 8, wherein said inspection mask support member and said positioning device comprise:
a base;
a first movable member disposed parallel to said base;
a second movable member disposed parallel to said first movable member;
a first sheet spring disposed perpendicularly to said base, and connecting one end of said first movable member to said base;
a first ball bearing interposed between said base, and the other end of said first movable member opposite said one end thereof, for movably supporting said other end of the first movable member;
a second sheet spring disposed perpendicularly to said base and said first sheet spring, for connecting one end of said second movable member to said first movable member;
a second ball bearing interposed between the other end of said second movable member opposite said one end thereof, and said first movable member, for movably supporting said other end of said second movable member;
a first actuator for moving said first movable member relative to said base, against an elastic force of said first sheet spring; and
a second actuator for moving said second movable member relative to said first movable member, against an elastic force of said second sheet spring.

11. An inspecting device according to claim 10, wherein each of said first and second actuators has a major portion which consists of a piezoelectric stack of a plurality of piezoelectric elements, said inspecting device further comprises a positioning controller for controlling said positioning device, said piezoelectric stack expanding and contracting in response to a change in a voltage applied thereto from said positioning controller.

12. An inspecting device according to claim 11, wherein said inspection mask support member and said positioning device include a first and a second encoder for detecting amounts of movement of said first and second movable members, respectively, and feeding back the detected amounts of movement to said positioning controller.

13. An inspecting device according to claim 8, wherein said inspection mask, said inspection mask support member, said optical system and said radiant energy converting means are joined to each other, and said positioning device is operable to move said inspection mask, inspection mask support member, optical system and radiant energy converting means as a unit.

14. An inspecting device according to claim 8, wherein said inspection mask, said inspection mask support member, said optical system and said radiant energy converting means are joined to each other, and said positioning device is operable to move said object support member and said at least one object relative to said inspection mask.

15. An inspecting device according to claim 8, further comprising a second positioning device operable in synchronization with said positioning device operable as a first positioning device, said second positioning device being connected to a lens system of said optical system for moving said lens system to permit the radiant energy transmitted through said translucent apertures, to be focused on a central part of each of said photoelectric converting elements.

16. An inspecting device according to claim 8, further comprising a second positioning device, and wherein said radiant energy converting means is fixed to a lens sytem of said optical system, said second positioning device being operable to move said radiant energy converting means together with said optical system.

17. An inspecting device according to claim 8, further comprising a second positioning device operable in synchronization with said positioning device operable as a first positioning device, said second positioning device being connected to said radiant energy converting means for moving said radiant energy converting means to permit the radiant energy transmitted through said translucent apertures, to be focused on a central part of each of said photo-electric converting elements.

18. An inspecting device according to claim 8, wherein said radiant energy is x-rays, and said optical system comprises a scintillator for converting the x-rays transmitted through said translucent apertures, into visible rays of light, said optical system further comprising a lens system through which said visible rays of light are imaged upon said photo-electric converting elements.

19. An inspecting device according to claim 8, wherein said memory means includes memory areas which are identified by addresses corresponding to said plurality of translucent apertures on said at least one object, said memory areas storing said first data indicative of said one photo-electric converting element corresponding to said defect, at a corresponding one of said addresses.

20. An inspecting device according to claim 8, wherein said memory means includes memory areas which are identified by addresses corresponding to said plurality of photo-electric converting elements, said memory areas storing said second data indicative of said relative position between said at least one object and said one aperture, at a corresponding one of said addresses.

21. An inspecting device according to claim 9, wherein said memory means stores said first position data, in combination with said second data which represents a position of said each aperture relative to said at least one object.

22. An inspecting device according to claim 8, wherein said inspection mask consists of a plurality of selectively used inspection masks having translucent apertures which are located at the same positions and which have different sizes, said inspecting device further comprising a programmable controller for controlling said positioning device so that an amount of intermittent movement of selected one of said inspection masks relative to said at least one object is adjusted depending upon the size of said translucent apertures of said selected inspection mask.

23. An inspecting device according to claim 8, wherein the number of said plurality of transparent apertures of said inspection mask is greater than the number of said plurality of patterns.

24. A device for detecting imperfections in a mask for x-ray lithography comprising:
an inspection mask to select positions in an x-ray mask under inspection by means of an x-ray aperture array thereon, the size of said x-ray apertures being chosen equal to a design rule of said x-ray mask under inspection, with two-dimensional spacing of said apertures in the array corresponding to that of an elementary inspection area array in said x-ray mask under inspection;
an alignment means for aligning a pair of regions of said x-ray mask under inspection with corrresponding positions of said x-ray aperture array, with an appropriate proximity gap;
a two-dimensional positioning means for moving said inspection mask to an assigned position designated by a two-dimensional "E-address" within said elementary inspection area in accordance with said design rule, keeping said proximity gap invariable;
a programmable driving means in said two-dimensional positioning means responsive to said E-address for covering an area equal to said elementary inspection area, with said x-ray aperture array covering the entire area of the x-ray mask under inspection;
an x-ray source to irradiate said x-ray mask under inspection with enough x-ray flux for high speed comparison;
a scintillation crystal having a size equal to said inspection mask to produce visible light energy within a given time interval, the total energy in said visible light being proportional to the x-ray energy passing through each of said x-ray apertures;
an image intensifying means for amplifying said visible light from said scintillation crystal;
a two-dimensional charge-coupled image sensing means to produce a serial signal proportional to the visible light intensity impinging on a light sensitive element array thereof, the two-dimensional spacing of said light sensitive element array corresponding proportionally to the spacing of said elementary inspection area array;
an optical imaging means for focusing said visible light from an output plane of said image intensifying means upon said light sensitive element array of said two-dimensional charge-coupled image sensing means;
a fast signal processing means to accomplish comparison between a pair of serial signals originating from each corresponding position of said pair of x-ray mask regions under inspection, and thus a series of "C-address" data which indicates location of an imperfection in accordance with the location of said light sensitive element of said two-dimensional charge-coupled picture sensing means, at an instant of material discrepancy between said serial signals, within one frame spacing of said two-dimensional charge-coupled picture sensing means corresponding to a fixed position of said inspection mask designated by an E-address; and
a memory means having addresses according to the E-address, each address retaining an imperfection message as a series of the C-address data given by said fast signal processing means.

* * * * *